US008137685B2

(12) United States Patent
Kitazono et al.

(10) Patent No.: US 8,137,685 B2
(45) Date of Patent: Mar. 20, 2012

(54) HYALURONIC ACID COMPOUND, HYDROGEL THEREOF AND JOINT TREATING MATERIAL

(75) Inventors: Eiichi Kitazono, Hino (JP); Hiroaki Kaneko, Hino (JP); Masaya Ito, Hino (JP); Chiaki Fukutomi, Hino (JP); Saki Tsuzuki, Musashino (JP); Yoshihiko Sumi, Hino (JP)

(73) Assignee: Teijin Limited, Osaka (JP)

( * ) Notice: Subject to any disclaimer, the term of this patent is extended or adjusted under 35 U.S.C. 154(b) by 869 days.

(21) Appl. No.: 10/577,154

(22) PCT Filed: Oct. 27, 2004

(86) PCT No.: PCT/JP2004/016285
§ 371 (c)(1),
(2), (4) Date: Apr. 26, 2006

(87) PCT Pub. No.: WO2005/040224
PCT Pub. Date: May 6, 2005

(65) Prior Publication Data
US 2008/0193538 A1    Aug. 14, 2008

(30) Foreign Application Priority Data

Oct. 29, 2003    (JP) .................... 2003-368540
Jul. 13, 2004     (JP) .................... 2004-205682
Sep. 22, 2004    (JP) .................... 2004-274775

(51) Int. Cl.
*C07H 11/04*    (2006.01)
*A61K 31/715*   (2006.01)
*A61P 19/02*    (2006.01)

(52) U.S. Cl. ............... 424/402; 424/422; 536/123.1
(58) Field of Classification Search .................. None
See application file for complete search history.

(56) References Cited

U.S. PATENT DOCUMENTS

| 4,582,865 | A | | 4/1986 | Balazs et al. |
| 4,605,691 | A | | 8/1986 | Balazs et al. |
| 4,937,270 | A | | 6/1990 | Hamilton et al. |
| 5,464,942 | A | * | 11/1995 | Sakurai et al. ............... 536/21 |
| 5,470,578 | A | * | 11/1995 | Aoki et al. ................... 424/450 |
| 5,603,872 | A | | 2/1997 | Margalit |
| 5,624,839 | A | * | 4/1997 | Yada et al. ................... 435/378 |
| 5,733,892 | A | * | 3/1998 | Sakurai et al. ............... 514/54 |
| 5,939,323 | A | | 8/1999 | Valentini et al. |

FOREIGN PATENT DOCUMENTS

| EP | 0 315 349 A1 | | 5/1989 |
| EP | 581282 B1 | * | 5/1999 |
| EP | 1044691 A2 | * | 10/2000 |
| JP | 60-130601 A | | 7/1985 |
| JP | 63-123392 A | | 5/1988 |
| JP | 2-234689 A | | 9/1990 |
| JP | 4-80201 A | | 3/1992 |
| JP | 5-236951 A | | 9/1993 |
| JP | 6-72893 A | | 3/1994 |
| JP | 7-97401 A | | 4/1995 |
| JP | 9-59303 A | | 3/1997 |
| JP | 11-509256 A | | 8/1999 |
| JP | 2000-212204 A | | 8/2000 |
| JP | 2001-293081 A | | 10/2001 |
| JP | 2002-529550 A | | 9/2002 |
| JP | 2003-528131 A | | 9/2003 |
| WO | WO 97/04012 A1 | | 2/1997 |
| WO | WO 00/27887 A2 | | 5/2000 |
| WO | 01/72283 A1 | | 10/2001 |
| WO | WO 01/72283 A1 | | 10/2001 |

OTHER PUBLICATIONS

Mats Brittberg, M.D., Anders Lindahl, M.D., PH.D., Anders Nilsson, M.D., PH.D., Claes Ohlsson M.D., PH.D., Olle Isaksson, M.D., PH.D., and Lars Peterson, M.D.,PH.D., Treatment of Deep Cartilage Defects in the Knee with Autologous Chondrocyte Transplantation, The New England Journal of Medicine, Oct. 6, 1994, vol. 331, No. 14, pp. 889-895.

Shigeyuki Wakitani, M.D., Tatsuhiko Goto, M.D., Stephen J. Pineda, M.D., Randell G. Young, D.V.M., Joseph M. Mansour, PH.D., Arnold I. Caplan, PH.D. and Victor M. Goldberg M.D., Mesenchymal Cell-Based Repair of Large, Full-Thickness Defects of Articular Cartilage, The Journal of Bone and Joint Surgery, Incorporated, vol. 76-A, No. 4, Apr. 1994, pp. 579-592.

Mitsuo Ochi, Yuji Uchio, Masatoshi Tobita, and Masakazu Kuriwaka;Current Concepts in Tissue Engineering Technique for Repair of Cartilage Defect; Artificial Organs, 25(3):172-179, Blackwell Science, Inc.

J. Aigner, J. Tegeler, P. Hutzler, D. Campoccia, A. Pavesio, C. Hammer, E. Kastenbauer, A. Naumann, Cartilage tissue engineering with novel nonwoven structured biomaterial based on hyaluronic acid benzyl ester, J. Biomed. Mater. Res. 42, 172-181 (1998).

Paola Brun, Giovanni Abatangelo, Marco Radice, Valentina Zacchi, Diego Guidolin, Daniela Daga Gordini, Roberta Cortivo, Chondrocyte aggregation and reorganization into three-dimensional scaffolds, J. Biomed. Mater. Res. 46, 337-346 (1999).

Luis A. Solchaga, Jung U. Yoo, Magnus Lundberg, James E. Dennis, Barbara A. Huibregtse, Victor M. Goldberg, and Arnold I. Caplan, Hyaluronan-based Polymers in the Treatment of Osteochondral Defects, Journal of Orthopaedic Research, 18:773-780 (2000).

W. M. Chen, J. Soria, C. Soria, M. Krimsky, S. Yedgar; Control of capillary formation by membrane-anchored extracellular inhibitor of phospholipase $A_2$, FEBS Letters 522 (2002) 113-118.

* cited by examiner

*Primary Examiner* — Shaojia Anna Jiang
*Assistant Examiner* — Bahar Schmidtmann
(74) *Attorney, Agent, or Firm* — Sughrue Mion, PLLC

(57) ABSTRACT

A hyaluronic acid compound which is a reaction product between hyaluronic acid and a phosphatidyl ethanolamine. This compound has biocompatibility and bio-safety, and can be formed into a hydrogel or molded form having a certain shape. Making use of these properties, it is used to treat a knee joint, prevent the accretion of a tissue after an operation and keep a skin wet.

9 Claims, 1 Drawing Sheet

Histological evaluation of rabbit's knee joint 8 weeks after an operation

HYALURONIC ACID COMPOUND, HYDROGEL THEREOF AND JOINT TREATING MATERIAL

TECHNICAL FIELD

The present invention relates to a hyaluronic acid compound which is a reaction product between hyaluronic acid and a phosphatidyl ethanolamine, a hydrogel thereof and a joint treating material.

BACKGROUND ART

A cartilage is one of a small number of blood vessel-free tissues in vivo, and it is said that it is difficult to reconstruct its original tissue. In order to suppress the occurrence of osteoarthritis based on the localized change of the cartilage to a morbid state, such as a cartilage defect caused by an external injury or dissecting osteochondropathy, various remedies have been tried.

Autologous chondrocytes implantation (ACI) in which only the cell of a chondrocyte obtained by sampling a mesenchymal stem cell from autologous chondrocytes or bone marrow cells and differentiating it, or the chondrocyte cultured in a scaffold is implanted to a cartilage defective region has been tried (refer to N Engl J Med. 331, 889-95 (1994), J Bone Joint Surg Am. 76, 579-92 (1994) and Artificial Organs. 25, 172-179 (2001)).

To culture an autologous chondrocyte in vitro, 3-D culture for creating an environment close to the environment in vivo is tried energetically, and a material which is recognized as safe in vivo, such as collagen, alginic acid or fibrin is used as a scaffold. As for collagen out of these, Ochi et al. have developed a method using aterocollagen and have started clinical tests (JP-A 2001-293081).

Although collagen exhibits bio-absorptivity, it has problems that it is difficult to completely remove its antigenicity and that the possibility of its infection with an unknown virus cannot be denied.

In contrast to this, hyaluronic acid is a constituent of an extracellular matrix forming the cartilage of a joint and having high affinity for the cartilage. Further, as hyaluronic acid can be formed by fermentation without a raw material derived from an animal, the possibility of infection with an unknown virus is low unlike collagen. Therefore, studies on the treatment of an injury to the cartilage of a knee using hyaluronic acid are now under way for regenerative medical treatment.

U.S. Pat. No. 5,939,323, J. Biomed. Mater. Res. 42, 172-81 (1998), J. Biomed. Mater. Res. 46, 337-46 (1999) and J. Orthop. Res. 18, 773-780 (2000) disclose benzyl esterified hyaluronic acid. JP-A 7-97401 discloses bisepoxide crosslinked hyaluronic acid. Further, U.S. Pat. No. 4,582,865 and U.S. Pat. No. 4,605,691 disclose divinylsulfone crosslinked hyaluronic acid, JP-A 60-130601 discloses formaldehyde crosslinked hyaluronic acid, and JP-A 60-130601 discloses formaldehyde crosslinked hyaluronic acid. Other hydrazide crosslinked hyaluronic acids are known.

However, crosslinking agents are used to improve the bio-absorptivity of hyaluronic acid in all of the above prior arts. Since these crosslinking agents are non-bioabsorptive, the safety of the agents is concerned, and a highly safe material for treating the cartilage of a joint is desired. The term "crosslinking" as used herein means not only chemical crosslinking by covalent bonding but also ion crosslinking by electrostatic interaction and physical crosslinking by van der Waals force or hydrophobic interaction.

DISCLOSURE OF THE INVENTION

It is an object of the present invention to provide a safe hyaluronic acid compound which has excellent bio-adaptability.

It is another object of the present invention to provide a hyaluronic acid compound which provides a hydrogel strong enough to be used in a region under a load in vivo.

It is still another object of the present invention to provide a molded form of the above hyaluronic acid compound which is insoluble in an aqueous medium.

It is a further object of the present invention to provide a joint treating material which is the above hyaluronic acid compound of the present invention.

Other objects and advantages of the present invention will become apparent from the following description.

According to the present invention, firstly, the above objects and advantages of the present invention are attained by a hyaluronic acid compound represented by the following formula (1):

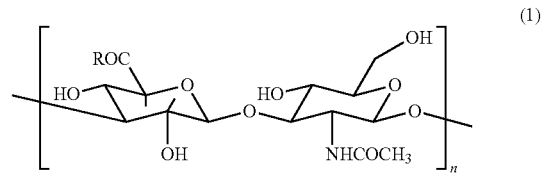

wherein R is a group represented by the following formula (1)-a, —OH or —ONa,

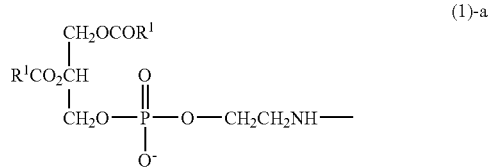

wherein $R^1$ is an alkyl group or alkenyl group having 10 to 28 carbon atoms, and n is an integer of 50 to 50,000, with the proviso that 1 to 100% of R is the group represented by the above formula (1)-a.

According to the present invention, secondly, the above objects and advantages of the present invention are attained by a hydrogel of the above hyaluronic acid compound of the present invention.

According to the present invention, thirdly, the above objects and advantages of the present invention are attained by a molded form of the above hyaluronic acid compound of the present invention.

According to the present invention, in the fourth place, the above objects and advantages of the present invention are attained by a joint treating material which is the above hyaluronic acid compound of the present invention.

BEST MODE FOR CARRYING OUT THE INVENTION

Figure 1:
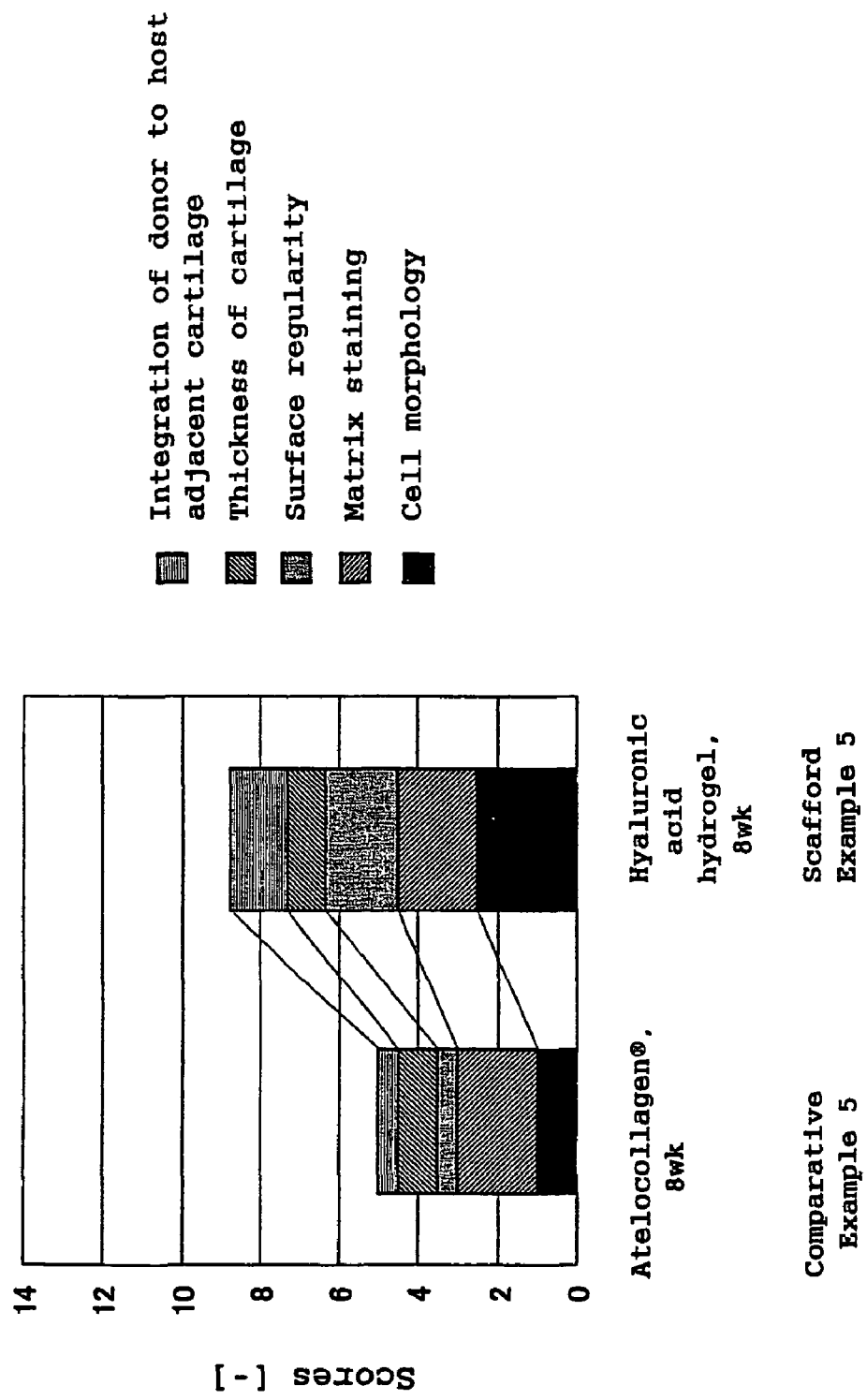
FIG. 1 shows the comparison of histological evaluation on the joint of rabbit's knee 8 weeks after an operation between Example 5 and Comparative Example 5.

The hyaluronic acid compound of the present invention is represented by the above formula (I). In the above formula (I), R is a phosphatidyl ethanolamino group represented by the formula (I)-a, —OH or —ONa. 1 to 100% of R must be a phosphatidyl ethanolamino group. When the phosphatidyl ethanolamino group accounts for less than 1% of R, the object of the present invention is not attained. $R^1$ is an alkyl group or alkenyl group having 10 to 28 carbon atoms, preferably 14 to 20 carbon atoms, and n is an integer of 50 to 50,000, preferably 300 to 30,000, more preferably 1,000 to 10,000.

Examples of the alkyl group having 10 to 28 carbon atoms represented by R include decyl, undecyl, lauryl, tridecyl, tetradecyl, pentadecyl, hexadecyl, heptadecyl, stearyl and eicosanyl. Examples of the alkenyl group having 10 to 28 carbon atoms include alkenyl groups having 1 to 3 carbon-carbon unsaturated bonds, corresponding to the above alkyl groups, such as oleyl group.

The compound represented by the above formula (I) is preferably a compound of the formula (I)-a in which two $R^1$CO-groups are oleoyl groups.

The hyaluronic acid compound represented by the above formula (I) can be prepared by reacting hyaluronic acid with a phosphatidyl ethanolamine.

The hyaluronic acid may be extracted from an animal tissue or manufactured by fermentation. A strain used in fermentation is a microorganism having the ability of producing hyaluronic acid which belongs to the genus *Streptococcus*, such as *Streptococcus equi* FM-100 (JP-A 63-123392) or *Streptococcus equi* FM-300 (JP-A 2-234689) all of which are known. What are prepared by culturing and refining variants thereof may also be used. The molecular weight of the hyaluronic acid is preferably about $1\times10^5$ to $1\times10^7$. The term "hyaluronic acid" as used herein includes alkali metal salts such as sodium, potassium and lithium salts of hyaluronic acid.

Further, the phosphatidyl ethanolamine may be extracted from an animal tissue or synthesized. Examples of the phosphatidyl ethanolamine include dilauroylphosphatidyl ethanolamine, dimyristoylphosphatidyl ethanolamine, dipalmitoylphosphatidyl ethanolamine, distearoylphosphatidyl ethanolamine, diarachidoylphosphatidyl ethanolamine, dibehenoylphosphatidyl ethanolamine, dilignoceroylphosphatidyl ethanolamine, dicerotioylphosphatidyl ethanolamine, dimontanoylphosphatidyl ethanolamine, dilaurooleoylphosphatidyl ethanolamine, dimyristooleoylphosphatidyl ethanolamine, dipalmitoylphosphatidyl ethanolamine, dioleoylphosphatidyl ethanolamine, dinervonoylphosphatidyl ethanolamine, diximenoylphosphatidyl ethanolamine, dilinolenoylphosphatidyl ethanolamine, dihiragonoylphosphatidyl ethanolamine, diarachidonoylphosphatidyl ethanolamine and didocosahexaenoylphosphatidyl ethanolamine. Out of these, dioleoylphosphatidyl ethanolamine is particularly preferred from the viewpoint of solubility.

The phosphatidyl ethanolamine is a substance safe for a living body and promotes the crosslinking such as physical crosslinking of hyaluronic acid as the hyaluronic acid compound of the present invention by making use of hydrogen bonding or hydrophobic interaction. Therefore, the hyaluronic acid compound of the present invention can be formed into a hydrogel or insoluble molded form which will be described hereinafter by the above crosslinking.

The amount of the phosphatidyl ethanolamine is preferably 1 to 100 equivalents based on 100 equivalents of the carboxyl group of hyaluronic acid. When the amount is smaller than 1 equivalent, the obtained hyaluronic acid compound does not form a hydrogel. When the amount is larger than 50 equivalents, the hydrophobicity of the formed hyaluronic acid compound becomes high and insoluble matter is formed, thereby making it difficult to form a hydrogel. Particularly when the amount is 51 equivalents or more, the formed hyaluronic acid compound shows high insolubility in an aqueous medium. It should be understood that the term "aqueous medium" as used herein means water, physiologic saline, a buffer solution or an aqueous solution containing an organic solvent such as an alcohol, and the term "insolubility" means that the hyaluronic acid compound resides in a living body for a certain period of time, gradually decomposes after that and is absorbed into the living body in the end.

When a compound is injected into the knee joint region of a living body under a load such as the knee joint of an animal, for example, a human being and has an elastic modulus of 200 Pa or less, it is difficult to maintain the shape of the compound. In contrast to this, as a hydrogel of the hyaluronic acid compound of the present invention has a high elastic modulus of 200 Pa or more, it is useful as a material for treating an injury to the cartilage of a knee.

When the hyaluronic acid compound of the present invention shows sufficiently high insolubility in an aqueous medium, it can be molded into a form, for example, a porous material such as sponge, nonwoven cloth or film. Even when the hyaluronic acid compound of the present invention is insoluble in an aqueous medium and its molded form is inserted into the body, it may be swollen with a body fluid after 2 or 3 weeks to become a gel.

To manufacture the molded form, freeze dry, dry film formation, wet film formation, coagulation spinning, span bonding, melt blowing and flush spinning methods may be employed.

Molded forms obtained by the above methods can be used in application fields which require the restoration of a cartilage by using as a molded form having a certain shape, particularly application fields which require high retentivity, as an agent for treating a joint, an agent for preventing the adhesion of a tissue after an operation or an agent for keeping a skin wet.

As described above, the hyaluronic acid compound of the present invention can be advantageously used as a joint treating material which has cartilage restoring ability.

EXAMPLES

The following examples are provided for the purpose of further illustrating the present invention but are in no way to be taken as limiting.

Sodium hyaluronate used in Examples 1 to 4 below is sodium hyaluronate derived from the genus *Streptococcus* and having an average molecular weight of 1,000,000, which is equivalent to a compound of the formula (1) in which n is 3,500. As for other reagents, tetrahydrofuran, 0.1M HCl, 0.1M NaOH, 1-ethyl-3-[3-(dimethylamino)propyl]-carbodiimide (EDC), 1-hydroxybenzotriazole (HOBt) and L-leucine methyl ester hydrochloride (of Wako Pure Chemical Industries, Ltd.), L-α-dioleoylphosphatidyl ethanolamine (COATSOME ME-8181) (of NOF Corporation) and 3% atelocollagen (of Koken Co., Ltd.) were used.

Example 1

110 mg (0.000033 mol) (10 equivalents based on 100 equivalents of the carboxyl group of hyaluronic acid) of L-α-dioleoylphosphatidyl ethanolamine was dissolved in 200 ml of a 1/1 solution of tetrahydrofuran and water (v/v). 500 mg of sodium hyaluronate was added to this solution, and 0.1 M HCl and 0.1 M NaOH were added to the resulting solution to adjust its pH to 6.8. 30 mg (0.000033 mol) of 1-ethyl-3-[3-(dimethylamino)propyl]-carbodiimide (EDC) and 25 mg (0.000033 mol) of 1-hydroxybenzotriazole (HOBt) were dissolved in 10 ml of a 1/1 solution of tetrahydrofuran and water, and the resulting solution was added to a reaction system and stirred through the night. After stirring, the obtained solution was purified by dialysis and freeze dried to obtain a product of interest. The formation of the product of interest was confirmed by $^1$HNMR (JNM-alpha400 of JEOL Ltd.).

30 mg of this freeze dried product was dissolved in 970 mg of ion exchange water to prepare a hydrogel having a concentration of 3 wt %. To measure the complex elastic modulus and shear yield stress of this hydrogel at 37° C., Rheometer RFIII, SRV (of TA Instrument Co., Ltd.) was used. The results are shown in Table 1. The term "complex elastic modulus" as used here means a constant indicative of the ratio of stress to strain of an elastic body, and the term "shear yield stress" means maximum stress at which the structure of a gel is maintained when shear stress is applied.

Example 2

The procedure of Example 1 was repeated except that 440 mg (0.00012 mol) (40 equivalents based on 100 equivalents of the carboxyl group of hyaluronic acid) of L-α-dioleoylphosphatidyl ethanolamine, 120 mg (0.000132 mol) of 1-ethyl-3-[3-(dimethylamino)propyl]-carbodiimide (EDC) and 100 mg (0.000132 mol) of 1-hydroxybenzotriazole (HOBt) were used. The results are shown in Table 1.

Comparative Example 1

A hydrogel was obtained by adding 5 ml of ion exchange water to 50 mg of sodium hyaluronate and stirring them. The evaluation of the physical properties of the hydrogel was carried out in the same manner as in Example 1. The results are shown in Table 1.

Comparative Example 2

Reworking experiments were conducted with reference to U.S. Pat. No. 4,937,270. A detailed description of the experiments is given below.

400 mg of sodium hyaluronate was dissolved in 40 ml of water and pH of the resulting solution was adjusted to 4.75 with 0.1M HCl.

153 mg (0.80 mmol) of 1-ethyl-3-[3-(dimethylamino)propyl]-carbodiimide (EDC) and 182 mg (1.0 mmol) of L-leucine methyl ester hydrochloride were added to the above solution and stirred for 5 hours. After stirring, the resulting solution was purified by dialysis and freeze dried to obtain a product of interest. The evaluation of the physical properties of the product of interest was carried out in the same manner as in Example 1. The results are shown in Table 1.

Comparative Example 3

Aterocollagen was measured under the same conditions as in Example 1 except that aterocollagen was used. The results are shown in Table 1.

TABLE 1

| | Material | Complex elastic modulus (Pa) | Shear yield stress (Pa) |
| --- | --- | --- | --- |
| Example 1 | L-α-dioleoylphosphatidyl ethanolamine hyaluronate (10 mol %) | 421 | 1,083 |
| Example 2 | L-α-dioleoylphosphatidyl ethanolamine hyaluronate (40 mol %) | 902 | 1,734 |
| Comparative Example 1 | Sodium hyaluronate | 5 | 18 |
| Comparative Example 2 | Crosslinked hyaluronic acid | 513 | 515 |
| Comparative Example 3 | Aterocollagen | 293 | 919 |

It is obvious from Table 1 that L-α-dioleoylphosphatidyl ethanolamine hyaluronate is superior to sodium hyaluronate and aterocollagen in terms of complex elastic modulus and shear yield stress. When it is compared with crosslinked hyaluronic acid, it exhibits the same or higher mechanical properties.

Example 3

100 mg of sodium hyaluronate was dissolved in 40 ml of a 1/1 solution of tetrahydrofuran and water (v/v). 154 mg (0.00021 mol) (70 equivalents based on 100 equivalents of the carboxyl group of hyaluronic acid) of L-α-dioleoylphosphatidyl ethanolamine was added to this solution, and 0.1M HCl and 0.1M NaOH were further added to the solution so as to adjust its pH to 6.8. 42 mg (0.000231 mol) of 1-ethyl-3-[3-(dimethylamino)propyl]-carbodiimide (EDC) and 35 mg (0.000231 mol) of 1-hydroxybenzotriazole (HOBt) were dissolved in 10 ml of a 1/1 solution of tetrahydrofuran and water (v/v), and the resulting solution was added to a reaction system. At this point, 0.1M NaOH was added to maintain pH of the reaction system at 6.8. Thereafter, the resulting mixture was stirred through the night, dialyzed for 3 days and freeze dried to obtain a product of interest (sponge). The formation of the product of interest was confirmed by $^1$HNMR (JNM-alpha400 of JEOL Ltd.)

A solubility test was conducted by the following method. 20 mg of the obtained product of interest was immersed in 5 ml of phosphoric acid buffer physiologic saline to carry out a solubility test for 4 weeks while the product was left to stand at room temperature and check its solubility visually. The results of the solubility test are shown in Table 2.

Example 4

A product of interest (sponge) was obtained in the same manner as in Example 1 except that 223 mg (0.0003 mol) (100 equivalents based on 100 equivalents of the carboxyl group of hyaluronic acid) of L-α-dioleoylphosphatidyl ethanolamine, 60 mg (0.00033 mol) of 1-ethyl-3-[3-(dimethylamino)propyl]-carbodiimide (EDC) and 50 mg (0.00033 mol) of 1-hydroxybenzo-triazole (HOBt) were used. The results of a solubility test are shown in Table 2.

Comparative Example 4

20 mg of sodium hyaluronate was immersed in 5 ml of phosphoric acid buffer physiologic saline to carry out a solubility test for 4 week while it was left to stand at room temperature and check its solubility visually. The results are shown in Table 2.

TABLE 2

| | Content of L-α-dioleoylphosphatidyl ethanolamine (equivalents)[1] | one day | one week | two weeks | four weeks |
|---|---|---|---|---|---|
| Example 3 | 70 | ○ | ○ | ○ | ○ |
| Example 4 | 100 | ○ | ○ | ○ | ○ |
| Comparative Example 4 | 0 | X | X | X | X |

○: not dissolved
Δ: partly dissolved
X: completely dissolved
[1]based on 100 equivalents of the carboxyl group of hyaluronic acid It is obvious from Table 2 that the insolubility in an aqueous liquid of L-α-dioleoylphosphatidyl ethanolamine hyaluronate (content: 70, 100 equivalents, respectively) is higher than that of sodium hyaluronate.

Disinfectant ethanol, a 10% neutral buffer formalin solution and a safranin O solution used in Example 5 below are commercially available products of Wako Pure Chemical Industries, Ltd., Fast Green FCF is a commercially available product of Polyscience Co., Ltd., ethylenediamine-N,N,N', N'-tetraacetic acid, tetrasodium salt and tetrahydrate (EDTA) are commercially available products of Dojin Kagaku Kenkyusho Co., Ltd., pentobarbital (to be referred to as "Nenbutal" hereinafter) is a commercially available product of Dainippon Pharmaceutical Co., Ltd., 1% xylokine is a commercially available product of Astra Zeneca Co., Ltd., crystal penicillin G potassium (to be referred to as "penicillin" hereinafter) is a commercially available product of Banyu Pharmaceutical Co., Ltd., and a tincture of iodine is a commercially available product of Yoshida Pharmaceutical Co., Ltd. A New Zealand white rabbit (to be referred to as "NZW rabbit" hereinafter) used in Example 5 was male, purchased from Nippon SLC Co., Ltd. and raised in a cage under normal conditions until its weight became 3.0 to 3.5 kg. The age of the rabbit after an operation was 24 to 28 weeks.

Example 5

The biological evaluation of the hyaluronic acid hydrogel having a concentration of 3 wt % prepared in Example 1 was carried out by the following method. Pentobarbital was administered to the articular vein of the NZW rabbit raised under normal conditions, and the following operation was made on the rabbit while it was generally anesthetized. Regions around the knee joint of a hind leg on both sides were shaved and disinfected with ethanol, and xylokine was administered several times locally and intramuscularly. The inner side of the knee joint was cut open and the femoral patella groove of the thighbone was exposed by dislocating the patella. A cylindrical defective region having an inner diameter of 5 mm and a depth of 5 mm was formed in the trochlear groove about 5 mm above the collateral ligament on the inner side with an operating drill to remove all the layer of the cartilage of the knee joint. The above obtained hydrogel was inserted into the defective region, and the patella was returned to its original position to suture the muscle. After penicillin was dropped on the affected part for the prevention of infection, the skin was sutured. Finally, the sutured part was disinfected with a tincture of iodine, and the rabbit was returned into the cage and raised under normal conditions. Eight weeks after the operation, it was euthanized to extract the defective region which was then immersed in a 10% neutral buffer formalin solution, fixed and evaluated histologically. The fixed tissue was degreased, decalcified with EDTA and wrapped in paraffin, and a portion near the center of the defective region was sliced on sagittal plane to prepare a sample. The prepared sample was dyed with safranin O and evaluated for the following items by used of score grades histologically.

Score grades used for the above histological evaluation were based on Makino T. et al., Kobe J Med Sci. 48:97-104 (2002) which is a modification of Wakitani S et. al., J Bone Joint Surg Am. 76, 579-92 (1994). Table 3 shows histological evaluation items and their scores.

The total score is 14 points, and the 3 to 5 grade system is employed according to evaluation items. As the restorability of the tissue becomes higher, that is, the tissue is restored to such an extent that it is close to a normal state, the score becomes close to 14 points. That is, the items are the restored Cell morphology (0 to 4 points), the matrix-staining (0 to 3 points), the surface regularity (0 to 3 points), the thickness of cartilage (0 to 2 points) and integration of donor with host (0 to 2 points). In this method, the score becomes higher as the tissue becomes closer to a normal state.

The results of histological evaluation by extracting the defective region 8 weeks after the operation are shown in FIG. 1. It was observed that the cartilage restored 8 weeks after the operation became an almost hyaline like cartilage and that a matrix was well produced. Connection with a normal region was satisfactory and the continuity of tissues was observed.

Comparative Example 5

A defective region was formed in the trochlear groove of the thighbone in the same manner as in Example 5, an atelocollagen gel (registered trademark) (type I of Koken Co., Ltd.) was inserted into the above region to restore it, and the defective region was extracted 8 weeks after the operation to make histological evaluation. The results are shown in FIG. 1.

When Comparative Example 5 is compared with Example 5, although there was no difference in the dyeability of the matrix between them, the surface was not smooth and the lower bone of the cartilage was not restored at all.

TABLE 3 histological evaluation on the defective region of cartilage

| A. Cell morphology | 4 hyaline cartilage |
| | 3 mostly hyaline cartilage |
| | 1 mostly noncartilage |
| | 0 noncartilage only |
| B. Matrix staining with safranin-O | 3 normal(compared to host) |
| | 2 slightly reduced |
| | 1 significantly reduced |
| | 0 no staining |
| C. Surface refularity* | 3 smooth (>3/4) |
| | 2 moderate(1/2 to 3/4) |
| | 1 irrefular(1/4 to 1/2) |
| | 0 severely irregular(<1/4) |
| D. Thickness of cartilage** | 2 > 2/3 |
| | 1 1/3 to 2/3 |
| | 0 < 1/3 |
| E. Integration of donor to host adjacent cartilage | 2 both edges integrated |
| | 1 one edge integrated |
| | 0 both edges not integrated |
| total A-E | 0-14 |

*Total smooth area of reparative cartilage compared to the whole area of the cartilage defect.
**Average thickness of reparative cartilage compared to that of surrounding cartilage.

It can be confirmed from the above results that Example 5 shows high restorability as a whole as the restored cartilage is almost close to a normal tissue in terms of the state of the surface and histological integrity to a normal tissue although it is equivalent to Comparative Example 5 in terms of the matrix staining and the thickness of the restored cartilage.

It is thereby found that the hyaluronic acid compound obtained from hyaluronic acid and phosphatidyl ethanolamine dioleoyl of the present invention is superior to Comparative Example (atelocollagen) as a cartilage treating material.

The invention claimed is:

1. A hyaluronic acid compound represented by the following formula (1)':

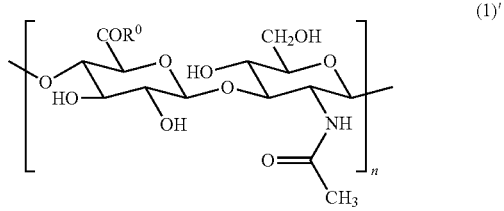

wherein $R^0$ is a group represented by the following formula (1)'-a, —OH or —ONa,

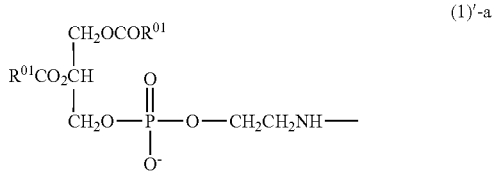

wherein $R^{01}$ is an alkenyl group having 10 to 28 carbon atoms, and n is an integer of 50 to 50,000, with the proviso that 1 to 50% of $R^0$ is the group represented by the above formula (1)'-a, said hyaluronic acid compound showing a complex elastic modulus of more than 200 Pa with its hydrogel having a concentration of 3 wt %.

2. The hyaluronic acid compound according to claim 1, wherein n is 300 to 30,000.

3. The hyaluronic acid compound according to claim 1, wherein two $R^{01}CO$-'s in the formula (1)'-a are both oleoyl groups.

4. A hydrogel of the hyaluronic acid compound of any one of claims 1 to 3.

5. A molded form of the hyaluronic acid compound of any one of claims 1 to 3.

6. The molded form of claim 5, wherein the molded form is a sponge, nonwoven cloth or film.

7. A joint treating material comprising a hyaluronic acid compound represented by the following formula (1)':

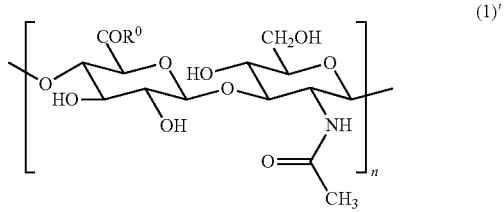

wherein $R^0$ is a group represented by the following formula (1)'-a, —OH or —ONa,

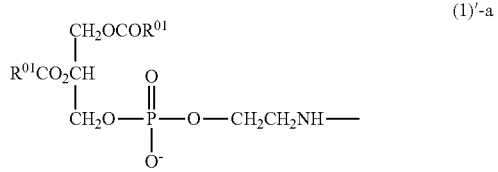

wherein $R^{01}$ is an alkenyl group having 10 to 28 carbon atoms, and n is an integer of 50 to 50,000, with the proviso that 1 to 50% of $R^0$ is the group represented by the above formula (1)'-a, said hyaluronic acid compound showing a complex elastic modulus of more than 200 Pa with its hydrogel having a concentration of 3 wt %.

8. The joint treating material according to claim 7, wherein $R^{01}$ is an alkyl group or alkenyl group having 14 to 20 carbon atoms and n is an integer of 1,000 to 10,000.

9. A method of using a hyaluronic acid compound comprising inserting a joint treating material prepared from a hyaluronic acid compound represented by the following formula (1)':

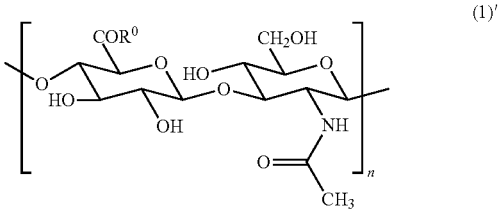

wherein $R^0$ is a group represented by the following formula (1)'-a, —OH or —ONa,

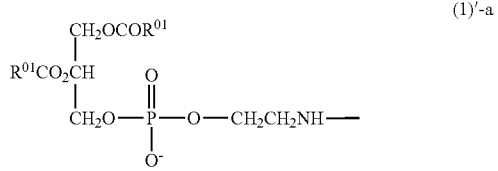

wherein $R^{01}$ is an alkenyl group having 10 to 28 carbon atoms, and n is an integer of 50 to 50,000, with the proviso that 1 to 50% of $R^0$ is the group represented by the above formula (1)'-a, said hyaluronic acid compound showing a complex elastic modulus of more than 200 Pa with its hydrogel having a concentration of 3 wt %, into the joint of a patient.

* * * * *